US012751787B2

(12) United States Patent
Yirga, II

(10) Patent No.: US 12,751,787 B2
(45) Date of Patent: Oct. 6, 2026

(54) MEDICAL SUPPORT AND SECURING DEVICE

(71) Applicant: John Andrew Yirga, II, Gates Mills, OH (US)

(72) Inventor: John Andrew Yirga, II, Gates Mills, OH (US)

( * ) Notice: Subject to any disclaimer, the term of this patent is extended or adjusted under 35 U.S.C. 154(b) by 415 days.

(21) Appl. No.: 18/385,040

(22) Filed: Oct. 30, 2023

(65) Prior Publication Data

US 2024/0138948 A1 May 2, 2024

Related U.S. Application Data

(60) Provisional application No. 63/420,624, filed on Oct. 30, 2022.

(51) Int. Cl.
*A61B 50/15* (2016.01)
*A61B 50/24* (2016.01)

(52) U.S. Cl.
CPC .............. *A61B 50/15* (2016.02); *A61B 50/24* (2016.02); *A61B 2050/155* (2016.02)

(58) Field of Classification Search
CPC .... A61B 50/15; A61B 50/24; A61B 2050/155
See application file for complete search history.

(56) References Cited

U.S. PATENT DOCUMENTS 2,175,500 A * 10/1939 Bemis .................... A47G 19/02 99/422
8,316,777 B1 * 11/2012 Rosing ................. A47B 23/046 108/50.01
9,635,933 B2 * 5/2017 Rosing ................. A47B 23/046
D850,833 S * 6/2019 Gevaert .......................... D6/700
D960,611 S * 8/2022 Iwasaki ...................... D6/656.13
D1,062,313 S * 2/2025 Yuan .......................... D6/656.15
D1,081,227 S * 7/2025 Davis ......................... D6/718.17
D1,091,163 S * 9/2025 Li .................................. D6/349
2014/0076316 A1 * 3/2014 Unger ................... F17C 13/084 128/205.12
2024/0138948 A1 * 5/2024 Yirga, II .............. A61G 12/001

* cited by examiner

*Primary Examiner* — Lee D Wilson
(74) *Attorney, Agent, or Firm* — Watts Law LLC

(57) ABSTRACT

A support securing device for securing objects during transport is provided that includes a first planar surface formed by the device's periphery and a second planar surface recessed within the first planar surface. A locking member having a locking end and a working end that during use is moveably nested within a passage located in the recess formed by the second planar surface. The locking member holds an object with the working end within and against a wall of the recess during use. A plurality of barbs extending from the locking end of the locking member selectively secure a pair of barbs to the passage along the locking end of the locking member and thereby securing the working end of the locking member against an object and a wall of the recess during use.

18 Claims, 14 Drawing Sheets

MEDICAL SUPPORT AND SECURING DEVICE

CROSS REFERENCES TO RELATED APPLICATIONS

The following application claims priority under 35 U.S.C. 119(e) to U.S. Provisional Patent Application Ser. No. 63/420,624 filed Oct. 30, 2022 entitled Medical Support and Securing Device. The above-identified application is incorporated herein by reference in its entirety for all purposes.

TECHNICAL FIELD

The present disclosure relates to a medical support and securing device for delivering items to a user that is standing needs tools or food, a person confined to a bed or in a lying position, patient, medical professionals, and the like. The medical support device is used to deliver items, for example, such as instruments, food, surgical tools, tools, and beverages to facilitate the ease of transferring of the items to a destination and to stabilize such items when on the medical support device.

BACKGROUND

Hospital tray food tables are well known as illustrated in FIG. 1. The tray food table is transferred under the patient's surgical bed or recovery bed as illustrated in FIG. 2. The tray food tables are rectangular in shape and have a planar surface to the periphery of all sides.

SUMMARY

One example embodiment of the present disclosure includes a support securing device is arcuately shaped.

In another example embodiment of the present disclosure a support securing device includes a first planar surface formed by the device's periphery and a second planar surface recessed within said first planar surface.

In another example embodiment of the present disclosure a support securing device is arcuately shaped and includes a first planar surface formed by the device's periphery and a second planar surface recessed within said first planar surface.

In another example embodiment, the second planar surface includes a passage for a locking device and a locking device to hold items within said recess.

In another example embodiment, the locking device includes a catch coupled to or formed with a stem, the stem having a number of uni-directional barbs to lock the catch of the locking device against an item to be secured from movement.

In another example embodiment, the locking device includes a catch coupled to or formed with a stem, the stem having a number of uni-directional barbs to lock the catch of the locking device against an item to be secured from movement, the barbs engaging once advanced through the passage against the recess.

While in another example embodiment, a support securing device for securing objects during transport is provided that includes a first planar surface formed by the device's periphery and a second planar surface recessed within the first planar surface. A locking member having a locking end and a working end that during use is moveably nested within a passage located in the recess formed by the second planar surface. The locking member holds an object with the working end within and against a wall of the recess during use. A plurality of barbs extending from the locking end of the locking member selectively secure a pair of barbs to the passage along the locking end of the locking member and thereby securing the working end of the locking member against an object and a wall of the recess during use.

In yet another example embodiment of the present disclosure includes a support securing device for securing items during transport, the support securing device comprising an arcuate first planar surface formed by the device's periphery and a second planar surface recessed within the first planar surface a locking member having a locking end and a working end that during use is moveably nested within a passage located in the recess formed by the second planar surface, the locking member holding object with the working end within and against a wall of the recess during use; and a plurality of elastic barbs extending from the locking end of the locking member to selectively secure a pair of barbs from the plurality of elastic barbs to the passage along the locking end of the locking member and thereby securing the working end of the locking member against an object and a wall of the recess during use.

BRIEF DESCRIPTION OF THE DRAWINGS

The foregoing and other features and advantages of the present invention will become apparent to one skilled in the art to which the present invention relates upon consideration of the following description of the invention with reference to the accompanying drawings, wherein like reference numerals refer to like parts unless described otherwise throughout the drawings and in which.

DETAILED DESCRIPTION

The present disclosure relates to a medical support and securing device 10 for delivering items to a user that is standing in need of tools, instruments, objects, or food, a person confined to a bed or in a lying position, patient, medical professionals, and the like. The medical support device 12 is used to deliver items, for example, such as instruments, food, surgical tools, tools, and beverages to facilitate the ease of transferring of the items to a destination and to stabilize such items when on the medical support device.

Figure 3:
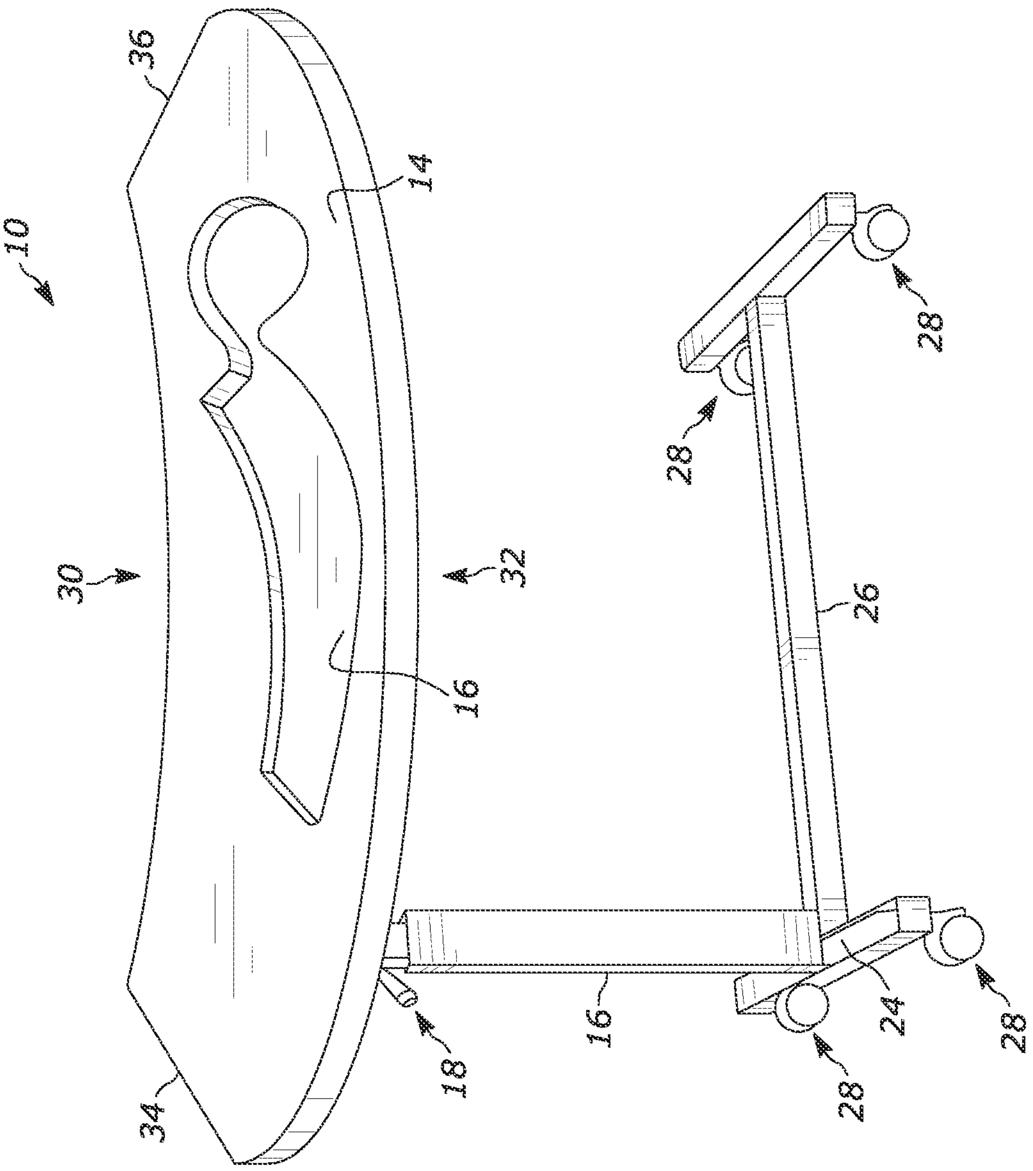
FIG. 3 illustrates a medical support and securing device constructed in accordance with a first example embodiment.

FIG. 3 illustrates a medical support and securing device 10 constructed in accordance with a first example embodiment. In the illustrated example embodiment, the medical support and securing device includes a first planar surface 14, and a second planar surface 16. The planar surfaces are supported by a support leg 16 that has a telescopic shaft and activation lever 18 for adjusting the heights of the planar surfaces. A support member 20 provides stability to the device 10 and includes two lateral bars 22, 24 spaced and connected by a longitudinal bar 26. Two casters 28 are fixed to each lateral bar to assist in moving transporting the device 10 across the floor as would be appreciated by one of ordinary skill in the art.

Figure 1:
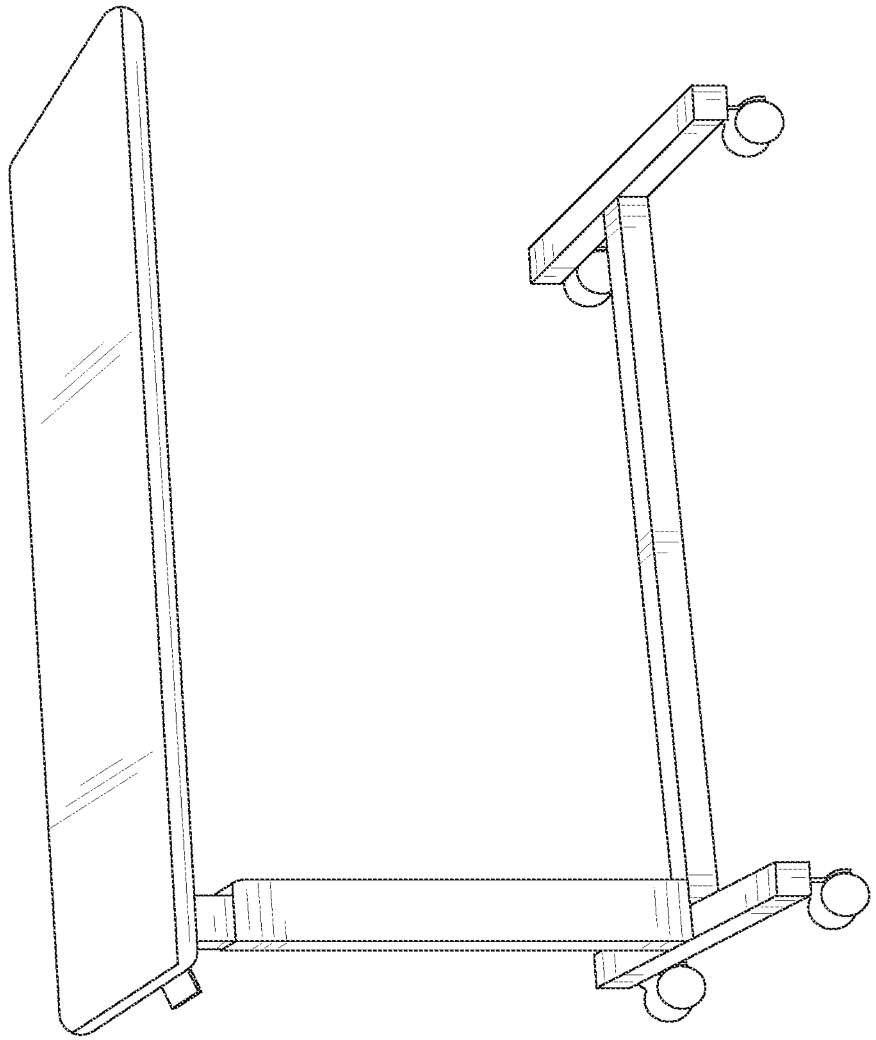
FIG. 1 (Prior Art)
FIG. 1 is an image known in the prior art.
Figure 2:
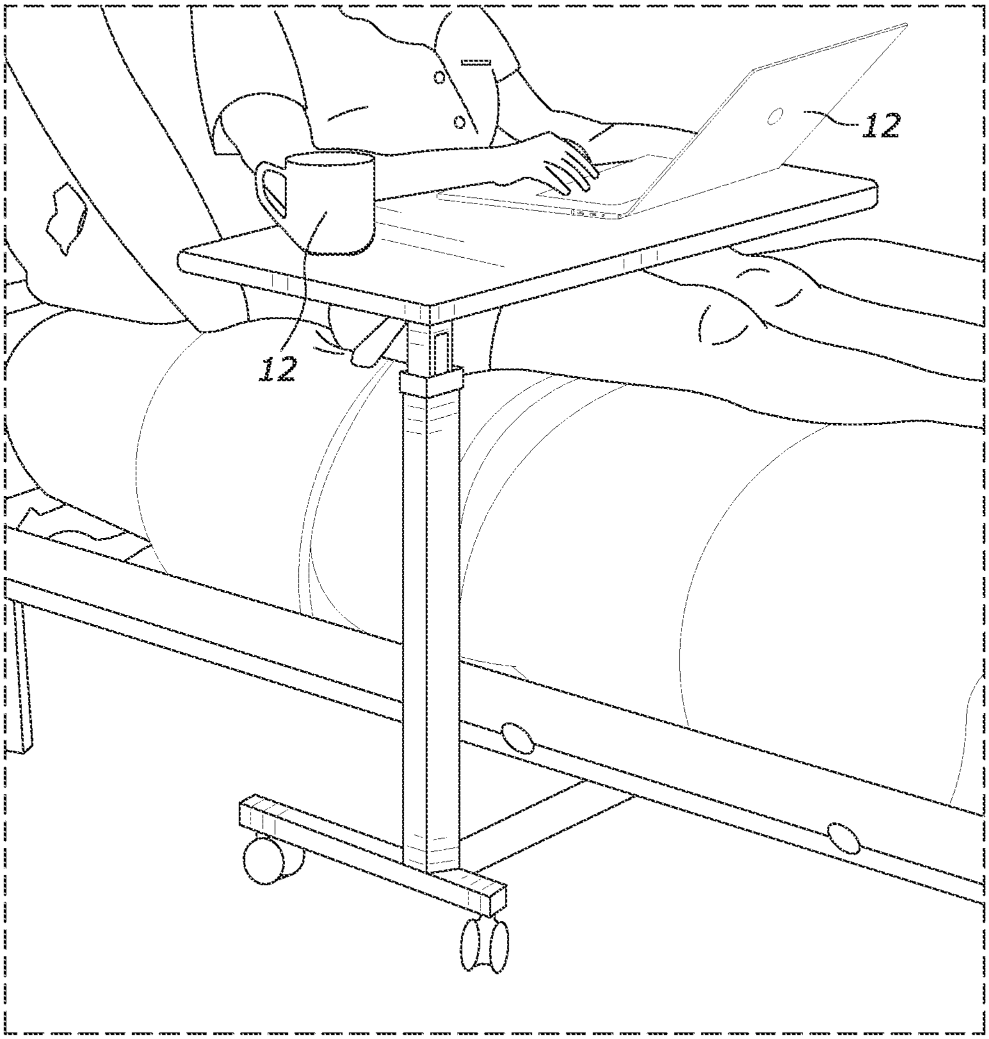
FIG. 2 (Prior Art)
FIG. 2 is an image known in the prior art.
Figure 4:
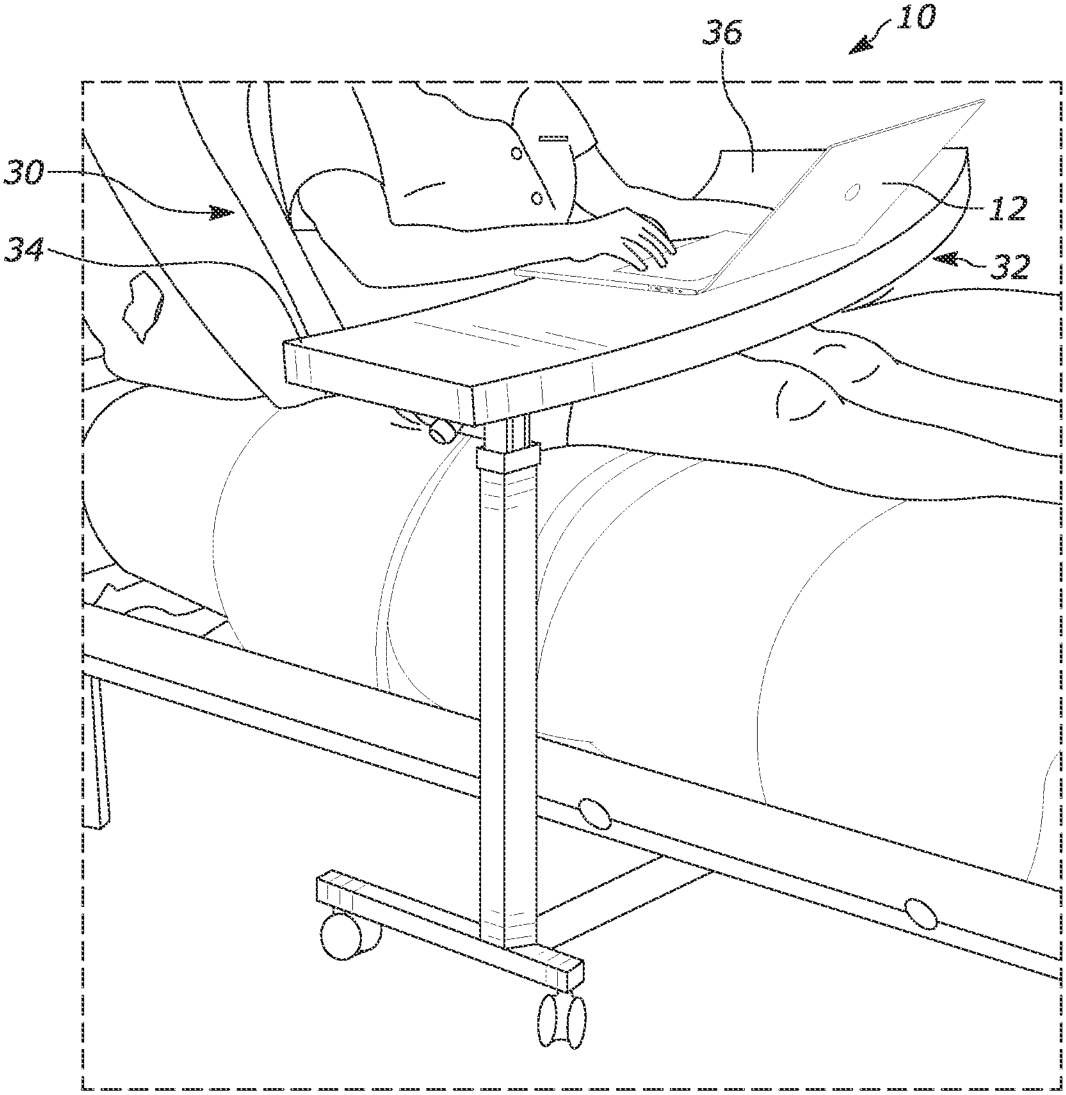
FIG. 4 illustrates a medical support and securing device constructed in accordance with another example embodiment.

FIG. 4 illustrates a medical support and securing device 10 constructed in accordance with another example embodiment. The medical support and securing device 10 includes a first arcuate edge 30 and a second arcuate edge 32 spaced by first and second ends 34 and 36, respectively. This arcuate shape of the device 10 allows the patient to be in close proximity to items supported by the device relative to those tables known in the prior art (see FIGS. 1 and 2).

Figure 5:
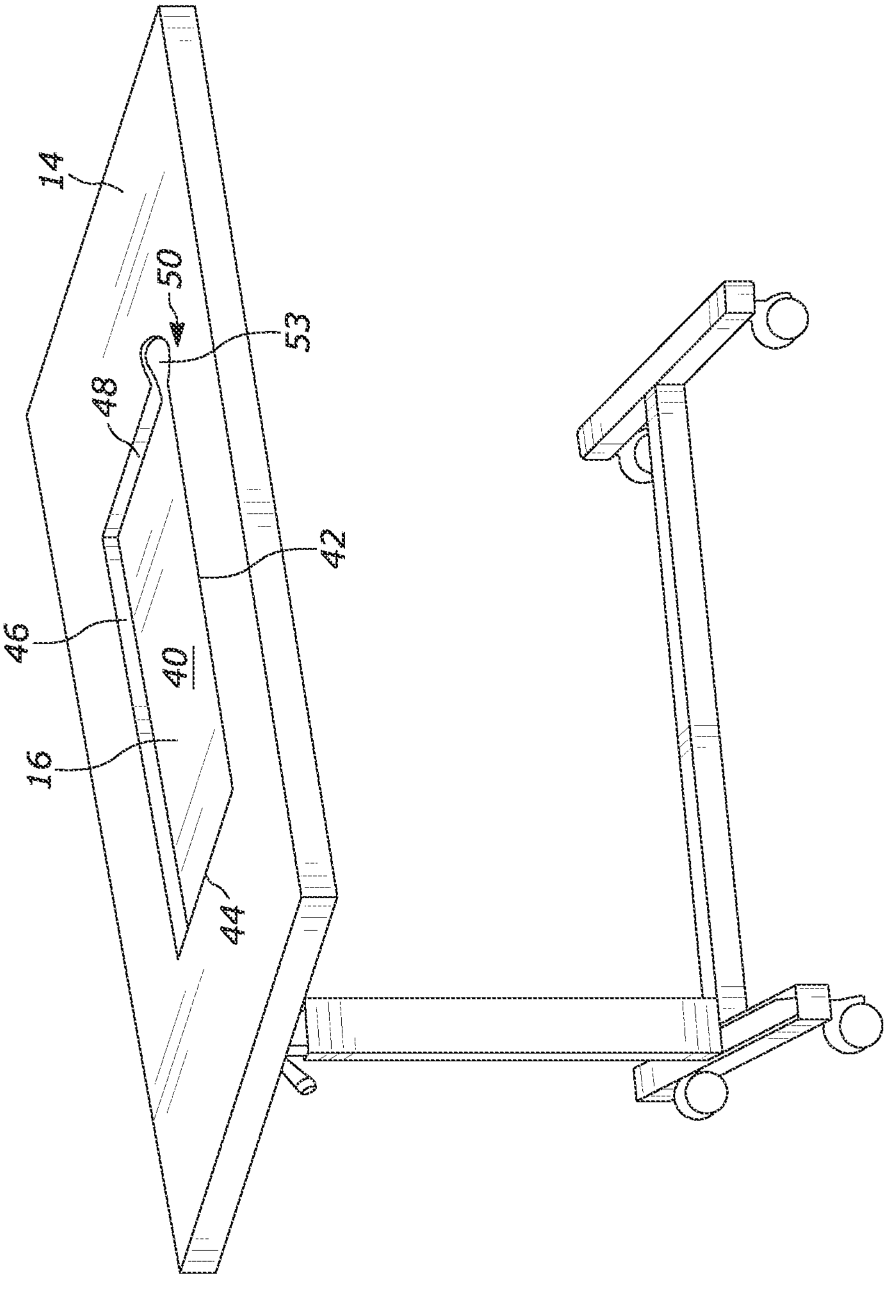
FIG. 5 illustrates a medical support and securing device constructed in accordance with another example embodiment.

FIG. 5 illustrates a medical support and securing device 10 constructed in accordance with another example embodiment. The medical support and securing device 10 includes a first planar surface 14, and a second planar surface 16 formed within a recess 40 of the first planar surface. The recess 40 in one example embodiment has an endless side or is circular, or in the illustrated example embodiment includes four sides, 42, 44, 46, 48. A passage 50 is formed to allow for a locking member or device 52 within one or two of the sides, 42, 44, 46, 48. In the illustrated example embodiment, the passage 50 is positioned between sides 42 and 48, but could equally be on a single side (see FIG. 6) without departing from the spirit and scope of the present disclosure.

Figure 6:
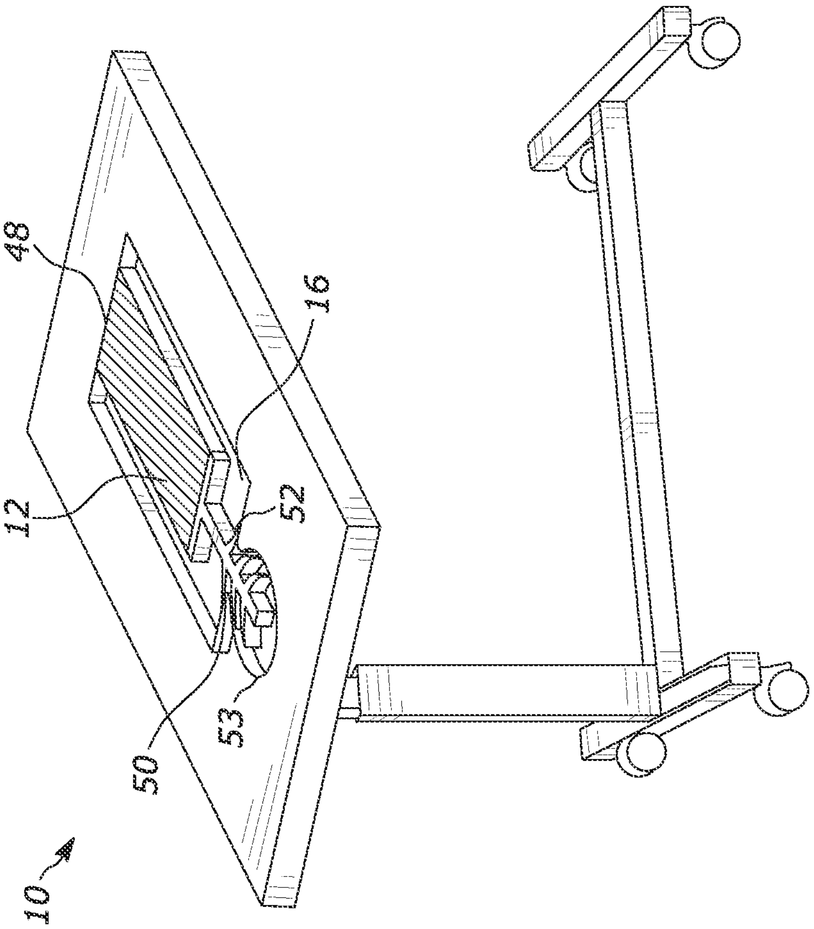
FIG. 6 illustrates a medical support and securing device constructed in accordance with another example embodiment.

FIG. 6 illustrates a medical support and securing device 10 constructed in accordance with another example embodiment wherein the device 10 illustrates the locking member 52 securing an item 12 within the recess 16 between the member and side 48. This prevents the movement of the item during transport of the device 10.

Figure 7:
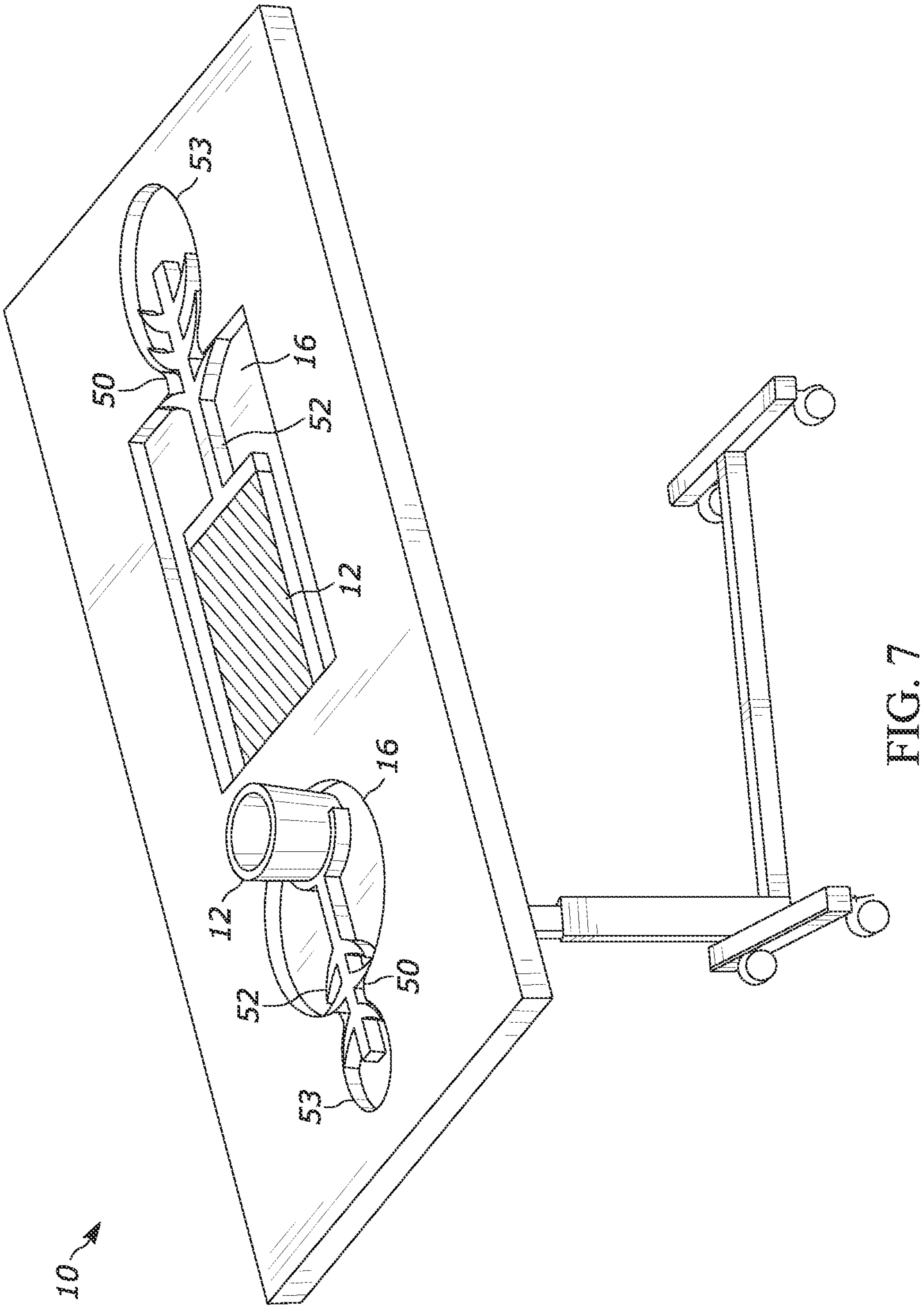
FIG. 7 illustrates a medical support and securing device constructed in accordance with another example embodiment.

FIG. 7 illustrates a medical support and securing device 10 constructed in accordance with another example embodiment. In FIG. 7 there are two recesses 16 one with multiple side and a single side. Both recesses have a passage 50 with a locking area 53 that allows for the locking member 52 to be advanced through the passage 50.

Figure 8:
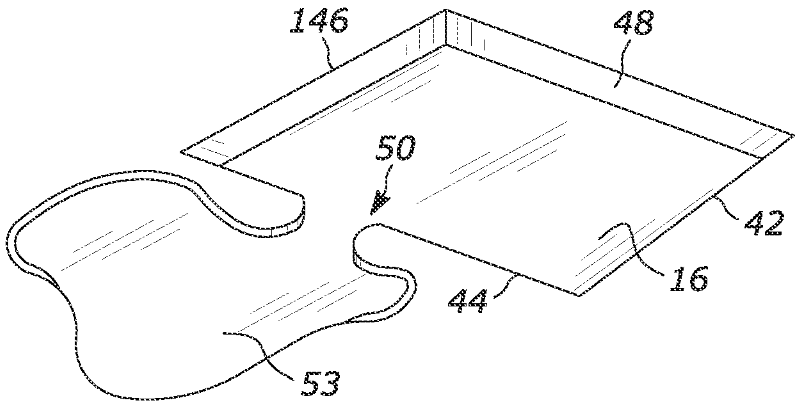
FIG. 8 illustrates a recess having a passage within the support and securing device.
Figure 9B:
FIG. 9B illustrates a left-side elevation view of the locking member in FIG. 9A, the right-side elevation view being a mirror image.
Figure 9A:
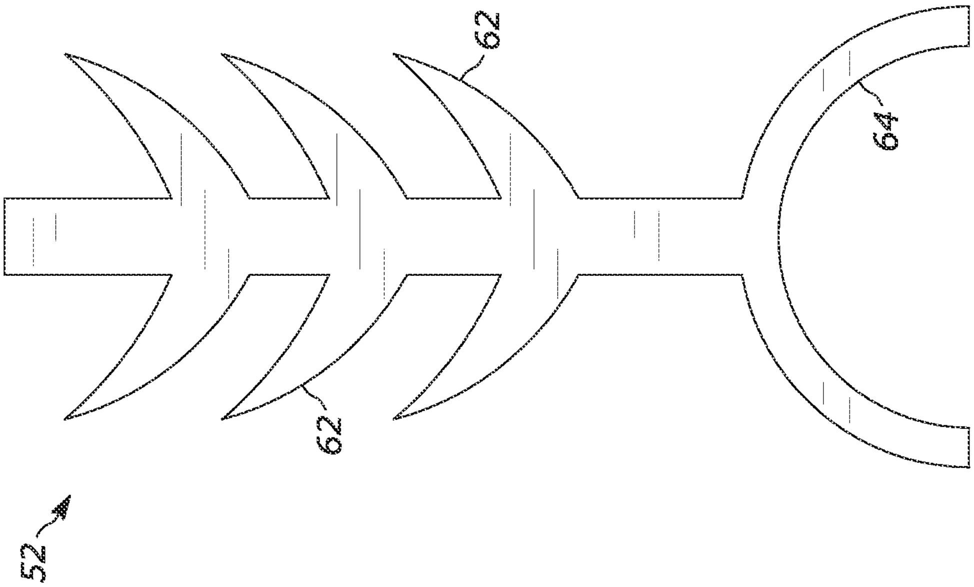
FIG. 9A illustrates a plan-view of a locking member constructed in accordance with one example embodiment.
Figure 9C:
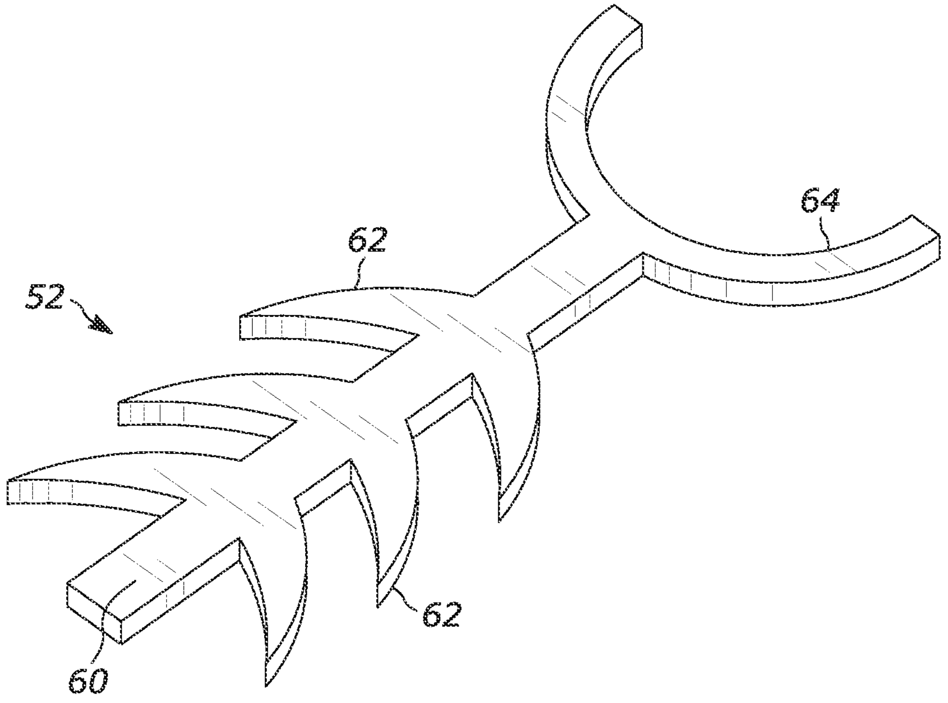
FIG. 9C illustrates a perspective view of the locking member in FIG. 9A.
Figure 9D:
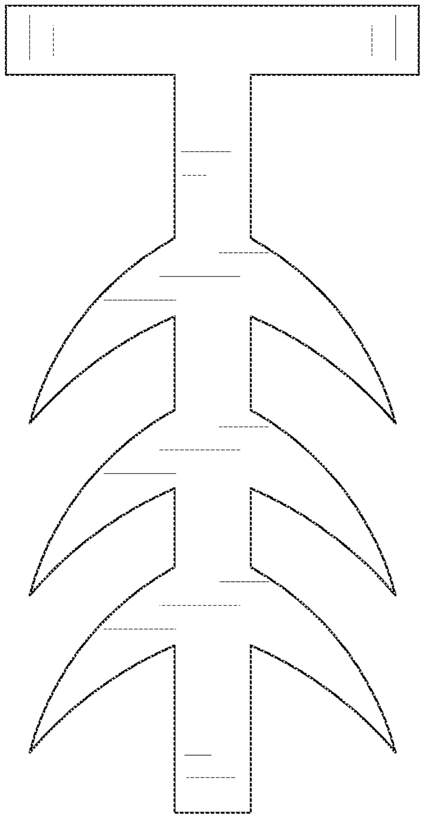
FIG. 9D illustrates a top plan view of a locking member in accordance with another example embodiment.

FIG. 8 illustrates a recess 16 having a passage 50 within the support and securing device 10;

FIG. 9 illustrates a locking member 52 constructed in accordance with one example embodiment. The locking member 52 includes a stem 60 and catch 64 spaced at one of two ends of the stem. In the illustrated example embodiment, the locking member 52 is made from a polymer such as plastic, polyethylene, polypropylene, rubber, metal, or any combination thereof. The locking member 52 includes a number of flexible barbs 62 that compress when passing through the passage 50 and expanding outward during the member's advancement through the passage. To lock the item 12 such as a cup or tray, the member 52 is advanced until the catch 64 engages the item 12 and pushes it against a side of the recess 16 so that the last barb pair is under pressure and recoiled against the passage 50. Because the barb pairs expand after existing the passage 50, they lock the item 12 into place as illustrated in FIGS. 6 and 7.

It will be appreciated by those of ordinary skill in the art after reviewing the present disclosure and accompanying drawings that the design of the locking member 52, passage 50, recesses 16, and locking area 53 include both functional and ornamental features designed by the sole inventor. Such ornamental features were selective for aesthetic purposes for the users or purchasers of the device 10.

Figure 10:
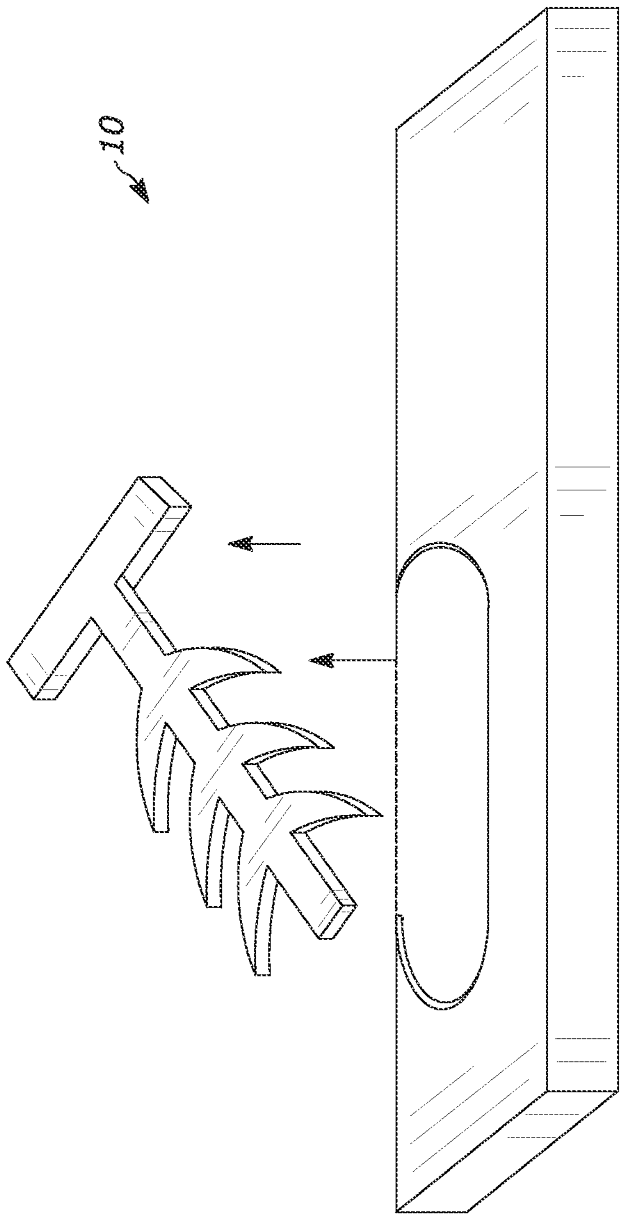
FIG. 10 illustrates a locking member being removed from the recess.
Figure 11:
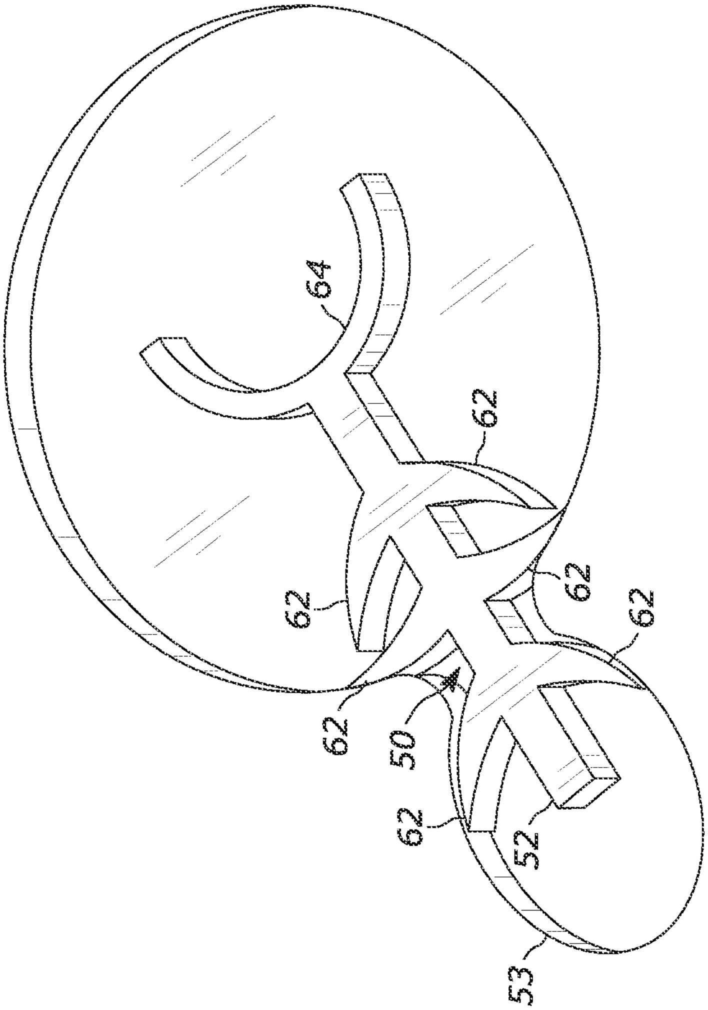
FIG. 11 illustrates a locking member constructed in accordance with one example embodiment.

FIG. 10 illustrates a locking member 52 being removed from the recess 16. The removal of the locking member 52 is achieved by raising the member upward away from the two planes 14 and 16, allowing the item 12 to again move freely.

Figure 12:
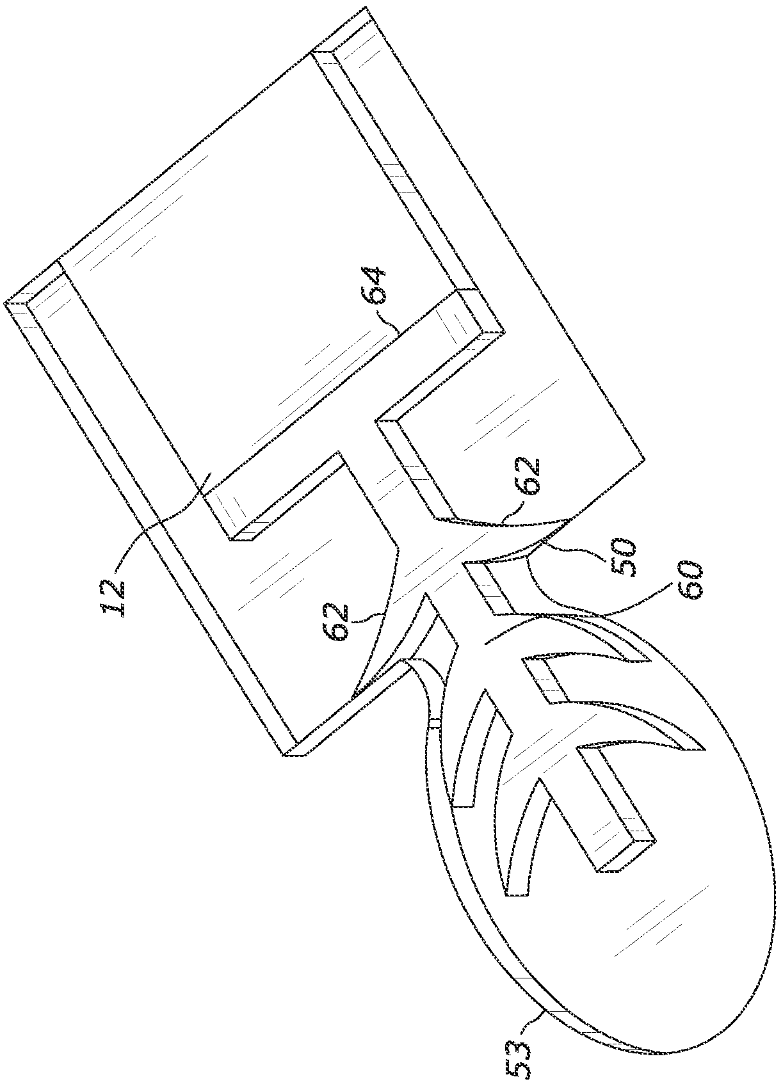
FIG. 12 illustrates the locking device being advanced to secure an item within the recess.

FIG. 12 illustrates the locking member 52 within the device 10 being advanced to secure an item 12 within the recess 16. While in one example the locking device 10 is securing a tray or a cup, it should also be appreciated it is used to secure surgical instruments during surgery, equipment, or machinery over a patient.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the spirit and scope of the appended claims.

What is claimed is:

1. A support securing device comprising: a first planar surface formed by a periphery of said securing device and a second planar surface formed within a recessed region within said first planar surface;

an elevated passage projecting from said recessed region for the movement of a locking member for holding items within said recessed region, said locking member removably positioned within said recessed region comprises a locking end and a working end;

said recessed region within said second planar surface further comprises a first recessed area and a second recessed area separated and spaced by said passage wherein said first and second recessed areas converge to said passage therebetween; and further wherein the locking member includes a catch coupled to or formed with a stem, the stem having a number of uni-directional barbs to lock the catch of the locking device against an item to be secured from movement.

2. The support securing device of claim 1 wherein the locking member includes a catch formed with a stem, the stem having a number of uni-directional barbs to lock the catch of the locking member against an item to be secured from movement, select barbs engaging said passage once advanced through the passage, depending on the size of the item to be secured against the recessed region.

3. The support securing device of claim 2 wherein said locking member when in a secured position is confined by a locking plane within the second planar surface and said passage.

4. A support securing device for securing items during transport, said support securing device comprising:

a first planar surface formed by the device's periphery and a second planar surface recessed within said first planar surface;

a locking member having a locking end and a working end that during use is moveably nested within a passage located in the recess formed by said second planar surface, said locking member holding an object with said working end within and against a wall of said recess during use; and a plurality of barbs extending from said locking end of said locking member to selectively secure a pair of barbs to the passage along the locking end of the locking member and thereby securing the working end of the locking member against an object and a wall of the second planar surface during use.

5. The support securing device of claim 4 wherein said device is arcuately shaped.

6. The support securing device of claim 4 wherein said barbs are made from a flexible polymer.

7. A support securing device for securing items during transport, said support securing device comprising:

an arcuate first planar surface formed by the device's periphery and a second planar surface recessed within said first planar surface;

a locking member having a locking end and a working end that during use the locking member is moveably nested within a passage located in the recess formed by said second planar surface, said locking member for securing an object with said working end within and against a wall of the second planar surface during use; and a plurality of elastic barbs extending from said locking end of said locking member to selectively secure a pair of barbs from said plurality of elastic barbs to the passage along the locking end of the locking member and thereby securing the working end of the locking member against an object and a wall of the second planar surface during use.

8. The support securing device of claim 7 wherein said recess is arcuately shaped.

9. The support securing device of claim 7 further comprising a second recess wherein said passage is a narrowed area providing an opening between said recess and said second recess.

10. The support securing device of claim 7 wherein said locking member is removably unsecured from the support securing device when said barbs are removed from contact with said passage.

11. The support securing device of claim 1 wherein said locking member is removably unsecured from the support securing device when said barbs are removed from contact with said passage.

12. The support securing device of claim 4 wherein said locking member is removably unsecured from the support securing device when said barbs are removed from contact with said passage.

13. The support securing device of claim 1 wherein said barbs are made from a flexible polymer.

14. The support securing device of claim 4 wherein said barbs are made from a flexible polymer.

15. A support securing device comprising: a first planar surface formed by a periphery of said securing device and a second planar surface formed within a recessed region within said first planar surface;

an elevated passage projecting from said recessed region for the movement of a locking member for holding items within said recessed region, said locking member removably positioned within said recessed region comprises a locking end and a working end;

said recessed region within said second planar surface further comprises a first recessed area and a second recessed area separated and spaced by said passage wherein said first and second recessed areas converge to said passage therebetween; and further wherein said locking member is removably unsecured from the support securing device when said barbs are removed from contact with said passage.

16. The support securing device of claim 15 wherein said barbs are made from a flexible polymer.

17. The support securing device of claim 15 wherein the locking member includes a catch formed with a stem, the stem having a number of uni-directional barbs to lock the catch of the locking member against an item to be secured from movement, select barbs engaging said passage once advanced through the passage, depending on the size of the item to be secured against the recessed region.

18. The support securing device of claim 17 wherein said locking member when in a secured position is confined by a locking plane within the second planar surface and said passage.

* * * * *